(12) United States Patent
Berquist

(10) Patent No.: US 6,767,562 B1
(45) Date of Patent: Jul. 27, 2004

(54) ORGANIC FUNGICIDE

(75) Inventor: Helen M. Berquist, Saratoga, CA (US)

(73) Assignee: Roseberg Investments, Inc., San Jose, CA (US)

( * ) Notice: Subject to any disclaimer, the term of this patent is extended or adjusted under 35 U.S.C. 154(b) by 0 days.

(21) Appl. No.: 10/365,561

(22) Filed: Feb. 11, 2003

Related U.S. Application Data

(60) Division of application No. 10/081,356, filed on Feb. 21, 2002, which is a continuation-in-part of application No. 09/715,536, filed on Nov. 17, 2000, now abandoned.

(51) Int. Cl.$^7$ ............................................. A61K 35/78
(52) U.S. Cl. ........................ 424/725; 424/729; 424/746; 424/766; 424/93.7; 424/405
(58) Field of Search ................................. 424/725, 746, 424/766, 405, 93.7, 729

(56) References Cited

U.S. PATENT DOCUMENTS

| | | | |
|---|---|---|---|
| 4,229,442 A | 10/1980 | Pinckard | 424/195 |
| 4,900,348 A | 2/1990 | Hoitink | 71/6 |
| 5,662,915 A | * 9/1997 | Okioga et al. | |
| 5,840,308 A | 11/1998 | Jassim et al. | 424/195.1 |
| 5,994,403 A | 11/1999 | Donatiello | 514/557 |
| 6,077,559 A | 6/2000 | Logan et al. | 426/650 |

FOREIGN PATENT DOCUMENTS

| | | |
|---|---|---|
| RU | 2067791 C1 | 10/1996 |

OTHER PUBLICATIONS

Arora et al., "In vitro studies on antifungal activity of tea and coffee against wood–rotting fungi", J. of Basic Microbiology, 1997, vol. 37, No. 3, pp. 159–165.
Chakraborty et al., "Accumulation of antifungal compounds in tea leaf tissue infected with Bipolaris carbonum", Folia Microbiologica, 1994, vol. 39, No. 5, pp. 409–414, abstract.
Demrow et al., "Administration of wine and grape juice inhibits in vivo platelet activity and thrombosis in stenosed canine coronary arteries", Circulation, 1995, vol. 91, No. 4, pp. 1182–1188, abstract.

Schwartz, H. F., "Soil–Borne Diseases of Onion", Colorado State University Cooperative Extension, Nov. 2, 2001, No. 2.940, pp. 1–6 (http://www..ext.colostate.edu/pubs/crops/02940.html).

Yegen et al., "Investigations on the fungitoxicity of extracts of six selected plants from Turkey against phytopathogenic fungi", Zeitschrift fuer Pflanzenkrankheiten and Pflanzenschultz, 1992, vol. 99, No. 4, pp. 349–359, abstract.

"Pythium ultimum".

Fitzpatrick et al., "Endothelium–dependent vasorelaxing activity of wind and other grape product", Am. J. Physiol., Aug. 1993, 265(2 Pt 2): H774–8, abstract.

Common Ayurvedic Herbs and Mineral, 1998, http://ww.thehimalayadrugco.com/cahv.htm, p. 1–4.

PDR for Herbal Medicines, 1998, Editors Gruenwald et al., p. 1113–1115.

Safety data for ferric dimethyldithiocarbamate http://phy-schem.ox.ac.uk/MSDS/FE/ferric–dimethyldithiocarbamate.html p. 1 of 1.

MSDS for Ferric Chloride Solution http://physchem.ox.ac.uk/MSDS/FE/ferric_chloride_solution p. 1 of 4.

* cited by examiner

Primary Examiner—Leon B. Lankford, Jr.
Assistant Examiner—Ruth A. Davis
(74) Attorney, Agent, or Firm—Thelen Reid & Priest, LLP; Adrienne Yeung

(57) ABSTRACT

The present invention is a fungicidal solution and method for controlling fungal disease in plants which provides for contacting the plant matter with a fungicidally effective application of an aqueous solution. The fungicidal solution is comprised of between about one-third (⅓) to two-third (⅔) cup of an organic plant matter to every two-third (⅔) gallon of a fermented solution. The organic solution may be any type of sage, tea leaves, coffee leaves, beech leaves, eucalyptus leaves, oak leaves, sumac leaves, and other similar leaves, or bark. The fermented solution contains between about (1%) one percent to (25%) twenty-five percent, per gallon, of an alcohol and grape juice.

13 Claims, 1 Drawing Sheet

ORGANIC FUNGICIDE

CROSS-REFERENCE TO RELATED APPLICATION

This application is a divisional of co-pending U.S. patent application Ser. No. 10/081,356, filed on Feb. 21, 2002, which is a continuation in part of U.S. patent application Ser. No. 09/715,536, entitled "ORGANIC FUNGICIDE" by inventor, Helen M. Berquist, filed Nov. 17, 2000, now abandoned.

FIELD OF THE INVENTION

This invention relates to fungicide, and more particularly to an organic fungicide for plants.

BACKGROUND OF THE INVENTION

Plants are constantly challenged by a wide variety of pathogentic organisms including viruses, bacteria, fungi, and menatodes. Attempts have been made to control plant disease by means of disinfections, replacement of the soil, various cultural practices, and control by chemicals. Some plants suffer from detrimental soil-spread diseases, which have not been possible to control owing to restrictions of use of chemical control agents and hazard periods due to possible residues or lack of sufficiently effective products.

The control of fungi is important since fungal growth on plants or on parts of plants inhibits production of foliage, fruit or seed, and the overall quality of a cultivated crop. About twenty-five (25) percent of all fungal diseases in agricultural and horticulture are caused by powdery mildew phytopathogens.

Due to the vast economic ramifications of fungal propagation in agricultural and horticultural cultivations, a broad spectrum of fungicidal and fungistatic products have been developed for general and specific applications. Such examples are the use of inorganic bicarbonate, carbonate compounds, lecithin, and lime. However, these fungicidal and fungistatic products may be harmful to the environment and may pollute areas such as ground waters. Thus, there is a need for an organic fungal treatment which provides for an inexpensive way to control fungi without harming the environment and protect the plants with a minimum of phytotoxic side effects.

These and other features and advantages of the present invention will be present in more detail in the following specification of the invention and in the associated figures.

SUMMARY OF THE INVENTION

The present invention is a fungicidal solution and method for controlling fungal disease in plants which provides for contacting the plant matter with a fungicidally effective application of an aqueous solution. The fungicidal solution is comprised of between about one-third ($\frac{1}{3}$) to two-third ($\frac{2}{3}$) cup of an organic plant matter to every two-third ($\frac{2}{3}$) gallon of a fermented solution. The organic plant may be any type of sage, tea leaves, coffee leaves, beech leaves, eucalyptus leaves, oak leaves, sumac leaves, and other plant leaves, or bark. The fermented solution contains between about (1%) one percent to (25%) twenty-five percent of alcohol such as ethanol, per gallon of organic plant solution.

The method of preparing the fungicidal solution comprises boiling a solution of at least two-third ($\frac{2}{3}$) cup of the organic plant matter in one-half ($\frac{1}{2}$) gallon of water, boiling down the solution to one-third ($\frac{1}{2}$) gallon, cooling and straining the solution, and adding at least two-third ($\frac{2}{3}$) gallon of a fermented solution to the solution.

BRIEF DESCRIPTION OF THE DRAWINGS

The accompanying drawings, which are incorporated in and constitute a part of this especification, illustrate one or more embodiments of the invention and, together with the present description, serve to explain the principles of the invention.

In the drawings.

DETAILED DESCRIPTION

Figure 1:
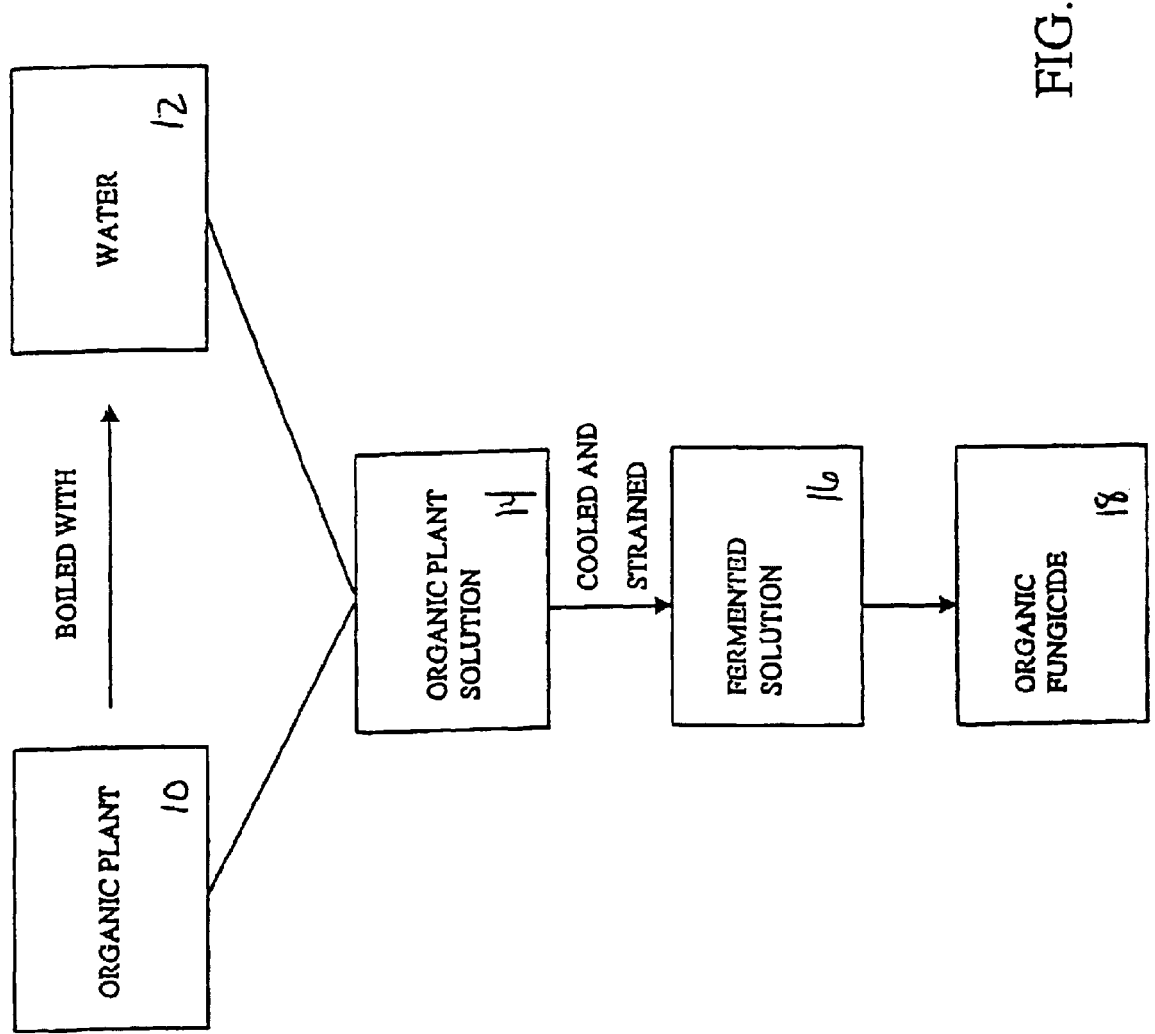
FIG. 1 shows one embodiment of the method of the present invention.

One embodiment of the present invention is described herein in the context of fungicides. Those of ordinary skill in the art will realize that the following description of the present invention is illustrative only and not in any way limiting. Other embodiments of the invention will readily suggest themselves to such skilled persons having the benefit of this disclosure.

In the interest of clarity, not all the routine features of the formulations described herein are described. It will of course be appreciated that in the development of any such actual implementation, numerous implementation-specific decisions must be made to achieve the user's specific goals, such as whether to use the solution in full strength or diluted. Moreover, it will be appreciated that such a development effort might be complex and time-consuming, but would nevertheless be a routine undertaking for those of ordinary skill in the art having the benefit of this disclosure.

The present invention is a fungicidal solution and method for controlling fungal disease in plants which provides for contacting the plant matter with a fungicidally effective application of an aqueous solution comprised of between about one-third ($\frac{1}{3}$) to two-third ($\frac{2}{3}$) cup of an organic plant matter to every two-third ($\frac{2}{3}$) gallon of a fermented solution.

In a preferred embodiment, the organic plant used is Salvia Officinalis or common sage. There are a variety of sages, such as Berggarten, Purpurascens, Icterina, Aurea, Big Sage (also known as Wild Sage Brush) and the like, that may be used. Sage is used for its bitter taste and strong smell.

As an alternative, organic plants with a high level of tannic acid, such as extracts of Camellia Sinensis or black tea leaves, may be used; tannic acid being one of the ingredients that kill and inhibit fungal growth due to its high acidity. In preparation for drying, the rolls of black tea leaves are allowed to "ferment" longer than any other tea leaves, which produces a higher level of tannin when extracted from the leaves. It is a useful source of tannic acid since it is easily massed produced and readily available. However, other leaves may also be used, such as coffee leaves, beech leaves, eucalyptus leaves, oak leaves, suman leaves, and the like.

Bark may also be used as the source of organic plant, such as the bark from an oak, hemlock, eucalyptus, mangrove, spruce, and other similar trees. The bark may also be obtained from the skin or root of shrubs or other woody plants.

A fermented solution is used in the fungicidal solution since the fermentation process adds sulphur dioxide to further inhibit and prevent the growth of bacteria and molds. In a preferred embodiment, grape juice is used as the fermented solution. Fermented grape juice is preferred since grapes carry their own microorganism or yeast, and have a variety of natural acids, tannic acid being one of the ingredients. Red grapes are the preferred grapes to use since it has a higher level of tannic acid than white grapes, however, other type of grapes may be used.

Referring to FIG. 1, in a preferred embodiment to prepare the fungicidal solution, two-third (⅔) cup of the organic plant 10 is boiled into one-half (½) gallon of water 12 and is boiled down to one-third (⅓) gallon 14 of an organic plant solution. The organic plant matter is preferably used in its solid mass form. However, those of ordinary skill in the art will now realize that tannic acid may be extracted from the organic plant matter if it is alternatively pulverized, powdered, chopped, minced or otherwise divided. The organic plant solution is then cooled and strained. The organic plant solution is then mixed into two-third (⅔) gallon of the fermented solution 16. Of course, the numbers may differ as to the amounts required based on each individual's needs such as for large commercial farmers. Moreover, the organic fungicidal solution 18 may be diluted with an aqueous medium; such as water, before use. In a preferred embodiment, the fungicidal solution is diluted by two percent (2%), or the solution may be used at full strength.

The fungicidal solution 18 may be applied to the plants by means such as by electrodynamic spraying means. When applying the solution, the area requiring treatment should be watered at least twelve (12) hours before treatment. For best results, the fungicidal solution should be applied either early morning or early evening, but not in the hot afternoon sun. Furthermore, although the fungicidal solution will not harm the taste of fruits or vegetables, it is best not to spray the fungicidal solution directly on the flowers of plants that feed bees and butterflies for obvious pollination reasons. The fungicidal solution should be applied all over the plants, including the trunk, stem, or deep roots of the trees, shrubs, or vines. Moreover, it is best not to water the treated area for forty-eight hours after applying the fungicidal solution 18.

The fungicidal solution 18 was tested for two years on a six and one-third (6⅓) acre estate located in the foothills of the Santa Cruz Mountains in the city of Saratoga, Calif. The vast variety of plants were treated for six months or until the plant appeared healthy. The temperature is a diverse degree of hot and cold and a variety of plants, trees, shrubs, and vines were tested. Examples of plants on which the fungicidal solution was tested on are Black and White Oak, Bay, Magnolia, London Plane Sycamore, Tulip Tree, Redwood, Roses, Maple Leaf Shrub, Camellias, Lavender, Daphne, Bird of Paradise, Boxwood, Wisteria, grass, and Pine. Numerous fruit, citrus, and vegetable plants, such as Weeping cherry, Per on, Pomegranate, Fig, Grapes, Tomato, Pepper, and many others were also tested using the fungicidal solution. The taste or appearance of the fruits and vegetables which were treated were not affected by the fungicide solution.

The plants showed no fungal growth and in fact showed remarkable growth and fruit. Plants that exhibited an overall unhealthy appearance (such as leaf blight, fungal growth on leaves and trunk, and brown spots on foliage) and treated with the fungicidal solution showed marked improvement and growth as well as the elimination of fungal growth throughout the plant's leaves and trunk. Of course, commercial growers should test a small portion of their crop before applying the fungicidal solution to the entire crop.

The fungicidal solution is not a substitute for fertilizer or water. Thus, fertilizer and water should still be applied to the plants. Although the fungicidal solution is to kill and prevent fungal growth on plants, the tests also indicated that it is a deterrent for animals, such as deer.

While embodiments and applications of this invention have been shown and described, it would be apparent to those of ordinary skill in the art having the benefit of this disclosure that many more modifications than mentioned above are possible without derparting form the inventive concepts herein The invention, therefore, is not to be restricted except in the spirit of the appended claims.

What is claimed is:

1. A method for preparing a fungicide solution, comprising:

boiling a solution of at least about two-thirds (⅔) cup of an organic plant matter in one half (½) gallon of water;

boiling down said solution to about one-third (⅓) gallon;

cooling said solution;

straining said solution; and adding at least about two thirds (⅔) gallon of a fermented solution to said solution, wherein said organic plant matter is selected from the group consisting of sage and tea leaves.

2. The method of claim 1 further comprising adding between about (1%) one percent to (25%) twenty-five percent of an alcohol per gallon of said fermented solution.

3. The method of claim 1 wherein said fermented solution contains grape juice.

4. The method of claim 1 further comprising diluting said fungicide solution in an aqueous medium.

5. A method for preparing a fungicide solution, comprising:

boiling a solution of a ratio of at least about one third (⅓) to about two thirds (⅔) cup of an organic plant matter in one half (½) gallon of water;

boiling down said solution to a ratio of about one third (⅓) gallon;

cooling said solution; and adding at least a ratio of about two thirds (⅔) gallon of a fermented alcohol solution to said solution;

wherein said organic plant matter is selected from the group consisting of sage and tea leaves.

6. The method of claim 5 further comprising adding a ratio of between about (1%) one percent to (25%) twenty-five percent, per gallon, of an alcohol to said fermented solution.

7. The method of claim 5 wherein said fermented solution contains grape juice.

8. The method of claim 5 further comprising diluting said fungicide solution in an aqueous medium.

9. A method for treating, inhibiting, and controlling plant fungal disease comprising contacting a plant with a fungicide solution comprising a ratio of about (⅓) one third to about (⅔) two thirds cup of an organic plant matter selected from the group consisting of sage and tea leaves, for about every (⅔) two thirds gallon of a fermented alcohol solution.

10. The method of claim 9 further comprising adding a ratio of between about (1%) one percent to (25%) twenty-five percent, per gallon, of an alcohol to said fermented solution.

11. The method of claim 9 wherein said fermented solution contains grape juice.

12. The method of claim 9 wherein said fungicide solution is applied to said plant (12) twelve hours after said plant is watered.

13. The method of claim 9 further comprising diluting said aqueous formulation for an effective application to said plant.

\* \* \* \* \*

UNITED STATES PATENT AND TRADEMARK OFFICE
CERTIFICATE OF CORRECTION

PATENT NO.        : 6,767,562 B1
APPLICATION NO.   : 10/365561
DATED             : July 27, 2004
INVENTOR(S)       : Berquist It is certified that error appears in the above-identified patent and that said Letters Patent is hereby corrected as shown below:

1) In column 1 line 18, replace "pathogentic" with --pathogenic--.

2) In column 1 line 19, replace "menatodes" with --nematodes--.

3) In column 2 line 3, replace "especification" with --specification--.

4) In column 2 line 49, replace "massed" with --mass--.

5) In column 2 line 51, replace "suman" with --sumac--.

6) In column 3 line 46, replace "Per on," with --Persimmon--.

7) In column 4 line 3, replace "form" with --from--.

Signed and Sealed this

Fifteenth Day of January, 2008

JON W. DUDAS
*Director of the United States Patent and Trademark Office*